(12) United States Patent
Koshinaka et al.

(10) Patent No.: US 12,216,752 B2
(45) Date of Patent: Feb. 4, 2025

(54) PERSONAL AUTHENTICATION DEVICE BASED ON ECHO SOUNDS, PERSONAL AUTHENTICATION METHOD, AND RECORDING MEDIUM

(71) Applicant: NEC Corporation, Tokyo (JP)

(72) Inventors: Takafumi Koshinaka, Tokyo (JP); Masahiro Saikou, Tokyo (JP); Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/611,775

(22) Filed: Mar. 21, 2024

(65) Prior Publication Data

US 2024/0232311 A1 Jul. 11, 2024

Related U.S. Application Data

(63) Continuation of application No. 17/887,338, filed on Aug. 12, 2022, now abandoned, which is a (Continued)

(30) Foreign Application Priority Data

Sep. 16, 2016 (JP) .................................. 2016-181897

(51) Int. Cl.
*G06F 21/00* (2013.01)
*A61B 5/117* (2016.01)
(Continued)

(52) U.S. Cl.
CPC .............. *G06F 21/32* (2013.01); *A61B 5/117* (2013.01); *H04L 63/0861* (2013.01);
(Continued)

(58) Field of Classification Search
CPC ....... G06F 21/32; A61B 5/117; A61B 5/7405; G07C 9/25; G07C 2009/00809;
(Continued)

(56) References Cited

U.S. PATENT DOCUMENTS

| 5,787,187 A | 7/1998 | Bouchard | G07C 9/37 382/115 |
| 8,187,202 B2 * | 5/2012 | Akkermans | G07C 9/37 382/115 |

(Continued)

FOREIGN PATENT DOCUMENTS

| JP | 2002-143130 A | 5/2002 |
| JP | 2004-013831 A | 1/2004 |

(Continued)

OTHER PUBLICATIONS

JP Office Action for JP Application No. 2023-009260, mailed on Mar. 12, 2024 with English Translation.

(Continued)

*Primary Examiner* — William A Corum, Jr.
(74) *Attorney, Agent, or Firm* — Sughrue Mion, PLLC

(57) ABSTRACT

Provided is a personal authentication device capable of simply securing security with little psychological and physical burden of a user to be authenticated. Personal authentication device includes: transmission unit that transmits a first acoustic signal to a user's head; observation unit that observes a second acoustic signal after the first acoustic signal propagation; calculation unit that calculates acoustic characteristics from the first and the second acoustic signal; extraction unit that extracts a feature amount related to a user from the acoustic characteristics; storage control unit that registers the feature amount in the storage unit; identification unit that identifies the user by collating the first feature amount with a second feature amount; and storage unit stores the first feature amount, wherein while identification (Continued)

unit identifies the user as being identical, transmission unit transmits the first acoustic signal every predetermined interval.

3 Claims, 11 Drawing Sheets

Related U.S. Application Data continuation of application No. 16/333,776, filed as application No. PCT/JP2017/032682 on Sep. 11, 2017, now abandoned.

(51) Int. Cl.
  *G06F 21/32* (2013.01)
  *H04L 9/40* (2022.01)
  *H04S 7/00* (2006.01)
  *G07C 9/37* (2020.01)
  *H04W 12/065* (2021.01)
  *H04W 12/65* (2021.01)

(52) U.S. Cl.
  CPC ...... *H04S 7/304* (2013.01); *G06F 2221/2117* (2013.01); *G07C 9/37* (2020.01); *H04W 12/065* (2021.01); *H04W 12/65* (2021.01)

(58) Field of Classification Search
  CPC .................. G10L 17/00; H04L 63/0861; H04L 2463/082; H04W 12/065; H04W 12/65
  See application file for complete search history.

(56) References Cited

U.S. PATENT DOCUMENTS

| | | | | |
|---|---|---|---|---|
| 9,277,334 | B1 | 3/2016 | Wong | H04R 25/606 |
| 9,558,523 | B1 | 1/2017 | Hodge | G06V 40/50 |
| 2007/0248242 | A1 | 10/2007 | Ritter | G07C 9/37 |
| | | | | 382/100 |
| 2008/0209547 | A1 | 8/2008 | Funahashi | G06F 21/78 |
| | | | | 726/20 |
| 2009/0097386 | A1 | 4/2009 | Miyauchi | G11B 20/00137 |
| | | | | 369/272.1 |
| 2009/0315675 | A1 | 12/2009 | Yokota | G06F 21/83 |
| | | | | 340/5.83 |
| 2010/0328033 | A1 | 12/2010 | Kamei | |
| 2011/0314530 | A1 | 12/2011 | Donaldson | |
| 2014/0282945 | A1 | 9/2014 | Smith et al. | |
| 2015/0156196 | A1 | 6/2015 | Kim | G02C 11/10 |
| | | | | 726/5 |
| 2017/0347180 | A1 | 11/2017 | Petrank | G06F 3/165 |
| 2018/0307818 | A1 | 10/2018 | Yano | G01N 29/11 |
| 2019/0258789 | A1 | 8/2019 | Koshinaka | G06F 21/32 |

FOREIGN PATENT DOCUMENTS

| | | |
|---|---|---|
| JP | 2004-065363 A | 3/2004 |
| JP | 2005-032056 A | 2/2005 |
| JP | 2006-119811 A | 5/2006 |
| JP | 2007-114992 A | 5/2007 |
| JP | 2008-033144 A | 2/2008 |
| JP | 2010-086328 A | 4/2010 |
| JP | 2012-161628 A | 8/2012 |
| JP | 2015-135669 A | 7/2015 |
| WO | 2007034371 A2 | 3/2007 |
| WO | 2009/016846 A1 | 2/2009 |
| WO | 2009/104437 A1 | 8/2009 |

OTHER PUBLICATIONS

Communication issued May 14, 2020 by the European Patent Office in application No. No. 17 850 850.3.
Communication dated Aug. 14, 2019, from the European Patent Office in European Application No. 17850850.3.
Written Opinion of the International Searching Authority of PCT/JP2017/032682 dated Nov. 21, 2017.
International Search Report of PCT/JP2017/032682 dated Nov. 21, 2017.
JP Office Action for JP Application No. 2023-009260, mailed on Jul. 2, 2024 with English Translation.

* cited by examiner

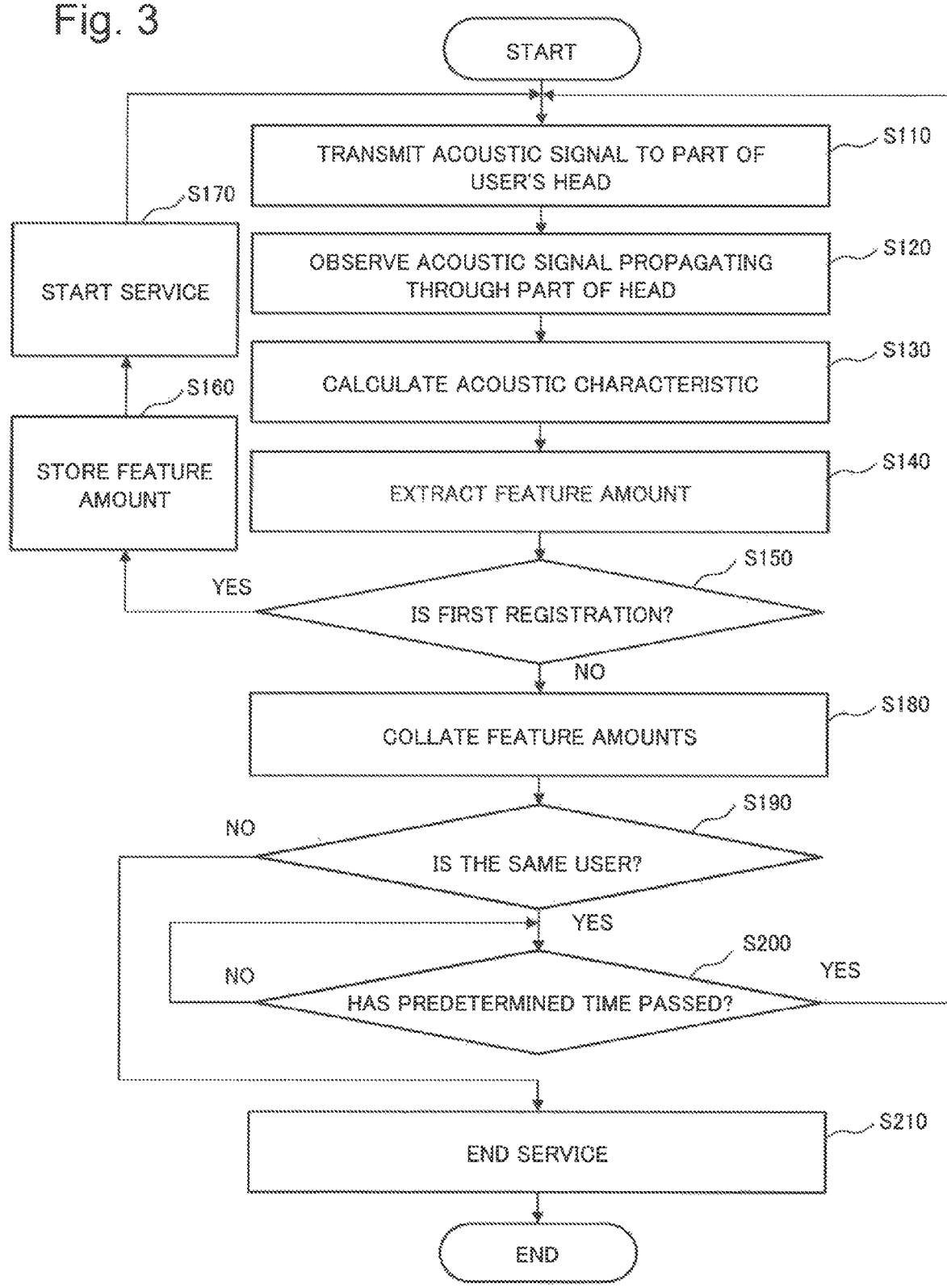

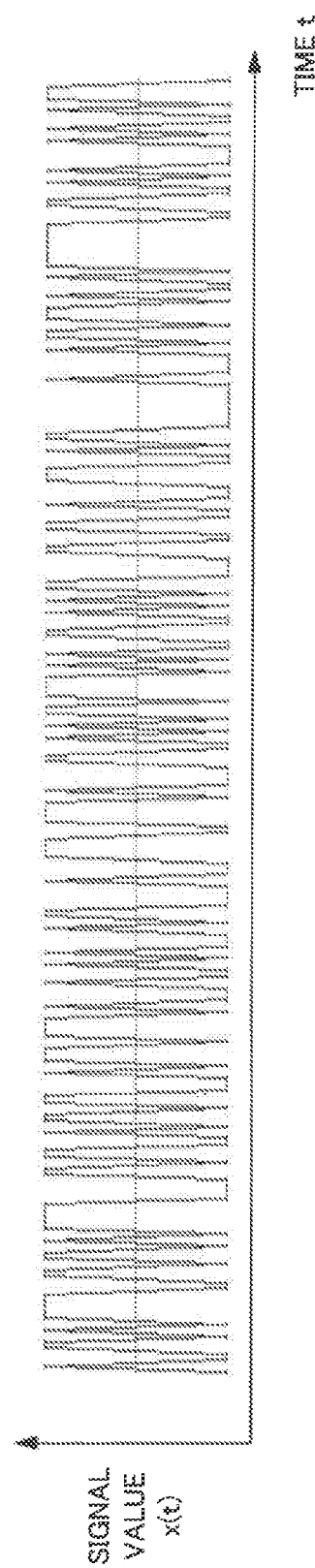

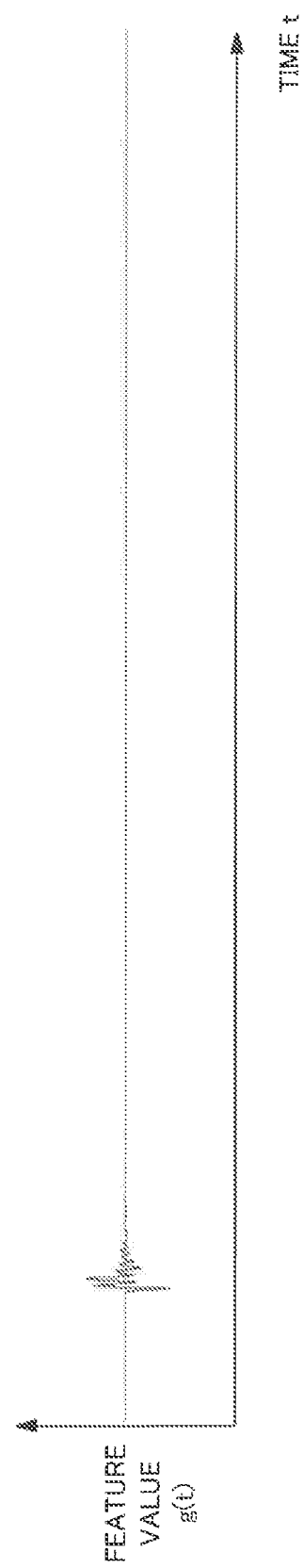

PERSONAL AUTHENTICATION DEVICE BASED ON ECHO SOUNDS, PERSONAL AUTHENTICATION METHOD, AND RECORDING MEDIUM

CROSS-REFERENCE TO RELATED APPLICATIONS

The present application is a continuation application of U.S. patent application Ser. No. 17/887,338 filed on Aug. 12, 2022, which is a continuation application of U.S. patent application Ser. No. 16/333,776 filed on Mar. 15, 2019, which is a National Stage Entry of international application PCT/JP2017/032682 filed on Sep. 11, 2017, which claims the benefit of priority from Japanese Patent Application No. 2016-181897 filed on Sep. 16, 2016, the disclosures of all of which are incorporated in their entirety by reference herein.

TECHNICAL FIELD

The present invention relates to a personal authentication device for authenticating an individual.

BACKGROUND ART

Since personal authentication (biometrics-based authentication) based on individual differences of a living body is less likely to leak or theft than passwords, it is increasingly introduced for the purpose of identifying individuals and confirming rights and for the purpose of security protection. As personal authentication technologies based on individual differences of a living body, there have been known technologies using e.g. a fingerprint, a vein, a face, an iris, and voice. Among them, a method using sound information can perform personal authentication with a general-purpose inexpensive device such as a telephone and a microphone without preparing a special device.

PTL 1 discloses a method in which a user is always monitored during log-in by using a biometrics authentication method based on a combination of a fingerprint, a face, a mouse movement.

PTL 2 discloses a method in which sound information received and transmitted from/to an auditory organ is subjected to signal processing, the processed information is stored in a storage device as acoustic characteristics, and the acoustic characteristics stored in the storage device and newly inputted acoustic characteristics are collated with each other, thereby determining whether a person to be authenticated is an authentication target person.

CITATION LIST

Patent Literature

[PTL 1] Japanese Unexamined Patent Application Publication No. 2004-13831 A
[PTL 2] Japanese Unexamined Patent Application Publication No. 2002-143130 A

SUMMARY OF INVENTION

Technical Problem

However, the biometric authentication disclosed in PTL 1 and performed at a predetermined place or time, has the following problems.

Firstly, in the case of personal authentication performed by acquiring biological information at a predetermined place or time, there is a problem that a user is forced to do an operation for performing authentication. For example, in the case of personal authentication using a fingerprint or a vein, an operation of a user such as putting his/her finger on a dedicated scanner is necessary. Furthermore, in the case of personal authentication using a face or an iris, an operation of a user such as turning a face to a camera is necessary. Furthermore, in the case of personal authentication using voice or bone conduction sound, an operation of a user such as speaking a password is necessary. Therefore, a user has a psychological and physical burden in each authentication. Moreover, in the case of personal authentication performed by acquiring biological information at a predetermined place or time, it is difficult to continuously authenticate a user (a person to be collated) at all times. Thus, when a user is intentionally replaced by another person after the authentication, since detecting the replacement is impossible, security level becomes low.

In the personal authentication method disclosed in PTL 2 and using an auditory organ, acoustic characteristics for identifying individual information need to be stored in a robust storage device in advance.

Therefore, in view of the aforementioned problems, the present invention aims to provide a personal authentication device capable of simply securing security with little psychological and physical burden of a user to be authenticated.

Solution to Problem

To solve the above problem, a personal authentication device according to first aspect of the present invention includes:
  a transmission means for transmitting a first acoustic signal to a part of a head of a user;
  an observation means for observing a second acoustic signal that is an acoustic signal after the first acoustic signal propagates through the part of the head of the user;
  a calculation means for calculating acoustic characteristics from the first acoustic signal and the second acoustic signal;
  an extraction means for extracting a feature amount related to the user from the acoustic characteristics;
  a storage control means for registering the feature amount in a storage means as a first feature amount; and
  an identification means for identifying the user by collating the first feature amount registered in the storage means with a second feature amount extracted from the extraction means after the first feature amount is registered,
  wherein, when the identification means identifies the user as being identical, the transmission means transmits the first acoustic signal every predetermined interval.

A personal authentication method according to second aspect of the present invention includes:
  transmitting a first acoustic signal to a part of a head of a user;
  observing a second acoustic signal that is an acoustic signal after the first acoustic signal propagates through the part of the head of the user;
  calculating acoustic characteristics from the first acoustic signal and the second acoustic signal;
  extracting a feature amount related to the user from the acoustic characteristics;

registering the feature amount in a storage means as a first feature amount; and identifying the user by collating the first feature amount registered in the storage means with a second feature amount extracted after the first feature amount is registered, wherein, when the user is identified as being identical, the first acoustic signal is transmitted every predetermined interval.

A personal authentication program according to third aspect of the present invention causes a computer to perform:

transmitting a first acoustic signal to a part of a head of a user;

observing a second acoustic signal that is an acoustic signal after the first acoustic signal propagates through the part of the head of the user;

calculating acoustic characteristics from the first acoustic signal and the second acoustic signal;

extracting a feature amount related to the user from the acoustic characteristics;

registering the feature amount in a storage means as a first feature amount; and identifying the user by collating the first feature amount registered in the storage means with a second feature amount extracted after the first feature amount is registered, wherein, when the user is identified as being identical, the first acoustic signal is transmitted every predetermined interval.

The personal authentication program may be stored in a non-transitory storage medium.

Advantageous Effects of Invention

According to the present invention, it is possible to provide a personal authentication device capable of simply securing security with little psychological and physical burden of a user to be authenticated.

BRIEF DESCRIPTION OF DRAWINGS

FIG. 3 is a flowchart illustrating an example of an operation of a personal authentication device according to a first example embodiment of the present invention.

FIG. 4A is a graph illustrating an example of a transmitted acoustic signal.

FIG. 5 is a graph illustrating an example of an impulse response as acoustic characteristics.

EXAMPLE EMBODIMENT

First Example Embodiment (Personal Authentication Device)

Figure 1:
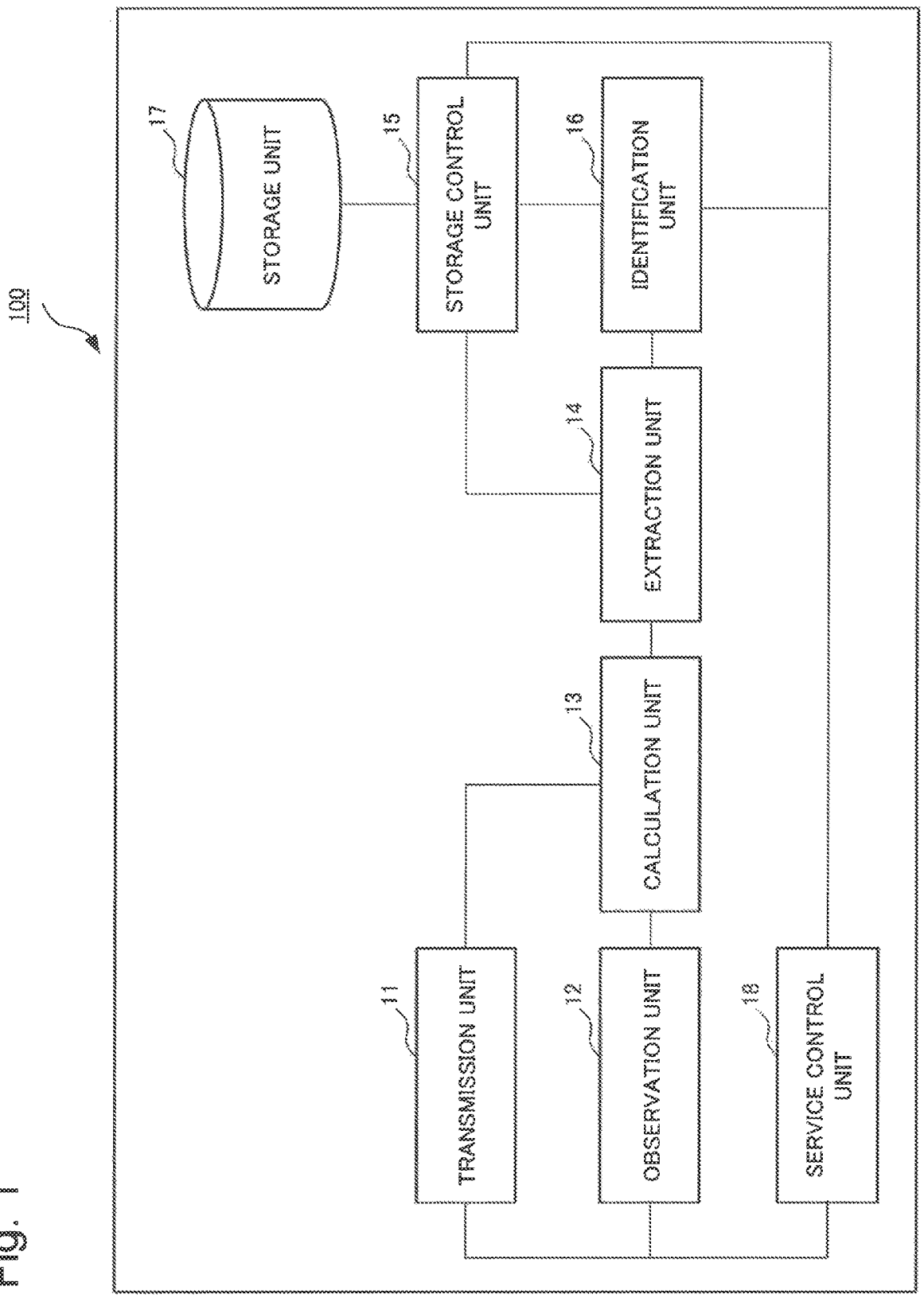
FIG. 1 is a block diagram illustrating a configuration example of a personal authentication device according to a first example embodiment of the present invention.

Personal authentication device 100 according to a first example embodiment of the present invention will be described with reference to the drawings. FIG. 1 is a block diagram illustrating a configuration example of personal authentication device 100 according to the first example embodiment. Personal authentication device 100 illustrated in FIG. 1 includes transmission unit 11, observation unit 12, calculation unit 13, extraction unit 14, storage control unit 15, identification unit 16, storage unit 17, and service control unit 18.

Transmission unit 11 transmits an acoustic signal to a part of a user's head. The part of the head, to which the acoustic signal is transmitted, is more specifically an area where a cavity has been formed in the head, and may be at least a part of an area where it is possible to mount or approximate an ornament or a device for producing a sound effect.

Observation unit 12 observes an acoustic signal after the acoustic signal transmitted from transmission unit 11 propagates through the part of the user's head. Furthermore, the part of the head serving as the propagation path of the acoustic signal may be more specifically at least a part of a skull, a brain, and a sensory organ constituting the head, and a cavity among them.

Calculation unit 13 calculates acoustic characteristics of the acoustic signal propagating through the part of the user's head on the basis of the acoustic signal transmitted from transmission unit 11 and the acoustic signal observed by observation unit 12.

Extraction unit 14 extracts a feature amount related to a user to be authenticated (an authentication target user) from the calculated acoustic characteristics. The extraction of the feature amount may be performed by a predetermined arithmetic operation.

Storage control unit 15 stores the feature amount obtained by extraction unit 14 in storage unit 17 at the time of registration of the authentication target user that is performed whenever a service is started (hereinafter, this may be described as first registration). Moreover, when each service is stopped, storage control unit 15 deletes the feature amount of the authentication target user from storage unit 17. That is, the feature amount serving as a password is stored and deleted for each service even in the case of the same user. As described above, a so-called one-time password method, in which a password is changed in a short period of time, is employed. Accordingly, it is not necessary to store a feature amount in storage unit 17 in advance. Moreover, a feature amount is stored in storage unit 17 whenever a service is provided, so that it is possible to secure high security.

Storage unit 17 stores the feature amount related to the authentication target user at the time of the first registration of the user. Hereinafter, a user, whose feature amount is stored in storage unit 17, may be called a registered user.

Identification unit 16 collates the feature amount obtained by extraction unit 14 with the feature amount stored in storage unit 17 at the time of the first registration, and determines whether these feature amounts coincide with each other (the user is identical).

Service control unit 18 controls the service provision. For example, service control unit 18 controls a service to be provided when the determination result of identification unit 16 indicates the same user, and controls the provision of the service to be stopped when the determination result does not indicate the same user. It should be noted that providing the service, for example, indicates starting application software for providing the service or maintaining a startup state of the application software and stopping the provision of the service indicates ending the application software.

Preferably, service control unit 18 receives permission, which indicates that a user is a legitimate user who can receive a service, from such as a service administrator before and after a feature amount is stored in storage unit 17 at the time of the first registration. In an example of the permission to accept a user, the service administrator inputs an instruction for permitting first registration to information processing device 1 to be described later, hands over earphone 4 to be described later to the user, and prompts the user to perform the first registration. It should be noted that the action of the service administrator may be mounted in service control unit 18 as a software program. For example, it may be possible to use a software program of another type of personal authentication (e.g. fingerprint authentication), which is highly burdensome for a user to carry out usual (continuous) authentication even though safety is high. In such a case, the administrator prompts input of a user via an input device such as a touch panel provided to or connected to the information processing device 1. The input for permitting the first registration by the service administrator may be performed by installing a physical switch at earphone 4 to be described later and mediating the switch.

Herein, the service in the present example embodiment is a service that does not need to identify user's personal information (such as a name), but should prohibit the service from being used by others or a service intended to detect the absence of a user. For example, the service includes a voice guidance service to be provided toward a specific person who wears earphone 4 in a specific place such as a department store, a museum, a conference with interpretation. In addition, the service also includes a movie or music appreciation service provided at fixed seats of the Shinkansen or airplanes, and a movie or music appreciation service distributed to an individual via a smart phone. It should be noted that design can also be changed for identifying a user.

Figure 2:
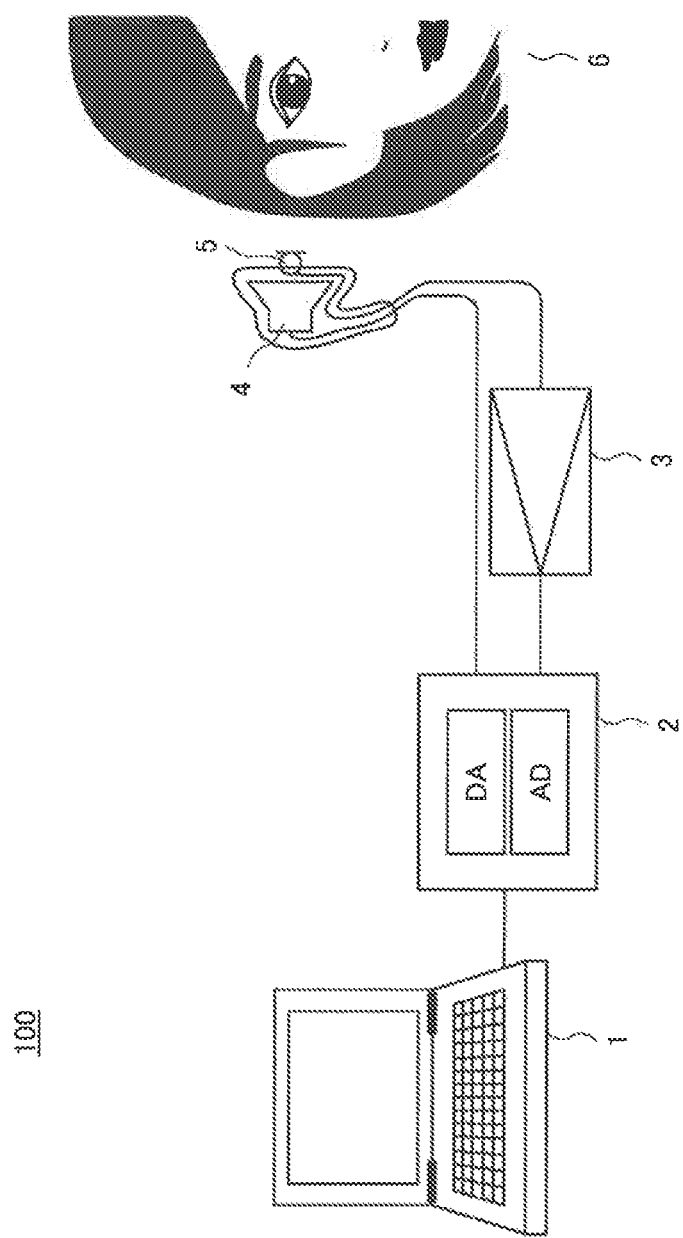
FIG. 2 is a configuration diagram illustrating a specific hardware configuration example of a personal authentication device according to a first example embodiment of the present invention.

FIG. 2 is a configuration diagram illustrating a specific hardware configuration example for implementing personal authentication device 100 of the present example embodiment illustrated in FIG. 1. Personal authentication device 100, for example, includes information processing device 1, sound processor 2, microphone amplifier 3, earphone 4, and microphone 5. Specifically, information processing device 1 is a smart phone, a tablet terminal, or a personal computer. Reference numeral 6 denotes a user to be recognized.

Sound transmitted from information processing device 1 is subjected to D/A (digital/analog) conversion in sound processor 2 and is delivered to earphone 4. Earphone 4 includes microphone 5. Earphone 4 is mounted on or inserted into a user's ear, sound produced by microphone 5 is echoed in the ear, and earphone 4 collects the echo sound. The collected echo sound is amplified by microphone amplifier 3, is subjected to A/D (analog/digital) conversion in sound processor 2, and is transmitted to information processing device 1.

In the hardware configuration example illustrated in FIG. 2, earphone 4 is an example of transmission unit 11. Furthermore, microphone 5, sound processor 2, and microphone amplifier 3 are an example of observation unit 12. As illustrated in FIG. 2, it is desired that microphone 5 and earphone 4 are integrated such that their relative positional relation does not change. However, when the relative positional relation therebetween does not change significantly, the present invention is not limited thereto. Furthermore, as an example of earphone 4 and microphone 5, a microphone-integrated earphone, in which they are inserted into the entrance of an ear canal, is used; however, as a practical example of both, a microphone may be set on a headphone that covers the auricle. Furthermore, as another practical example of both, a microphone may be installed in a handset part of a telephone. In addition, an acoustic signal transmitted by an earphone installed at the entrance of the ear canal of the left ear may be observed with a microphone installed at the entrance of the ear canal of the right ear, or vice versa.

It should be noted that the extraction of the feature amount may be performed from both ears or from the right or left ear only. In the present example embodiment, during a predetermined operation requiring personal authentication, a user is required to wear earphone 4 at all times. Thus, in the case of a predetermined operation over a long period of time, it is also assumed that a user experiences pain or a sense of discomfort in the ear. In such a case, the user may appropriately change an ear with earphone 4 to the other ear. It should be noted that when changing an ear to be authenticated, a first registration operation to be described later is necessary again.

Furthermore, calculation unit 13, extraction unit 14, identification unit 16, and service control unit 18 are respectively implemented by a central processing unit (CPU) and a memory operating according to a program in information processing device 1. Furthermore, storage unit 17 is implemented by a storage medium such as a hard disk in information processing device 1. The same function may also be performed by mounting a miniaturized information processing device 1 in earphone 4.

(Operation of Personal Authentication Device)

Next, an example of the operation of personal authentication device 100 in the present example embodiment will be described with reference to the flowchart illustrated in FIG. 3. Firstly, a service administrator inputs a keyword that permits first registration from a switch or a keyboard of information processing device 1 while facing a user, and prompts the user to register for the first time. On the basis of an operation of the user, the first registration is performed as follows, and subsequently, personal authentication device 100 performs a personal authentication operation as follows.

That is, in step S110, when the user wears earphone 4 in his/her ear, transmission unit 11 transmits an acoustic signal toward a part of a head of the user to be authenticated. For example, in step S110, earphone 4 transmits an acoustic signal toward an ear canal from the entrance of the ear canal. As the acoustic signal, a method using, such as, an M-sequence signal (maximal length sequence), a time stretched pulse (TSP) signal a widely used for measuring an impulse response is considered.

FIG. 4A is a graph illustrating an example of the acoustic signal transmitted by transmission unit 11. In the graph of FIG. 4A, a horizontal axis denotes time t and a vertical axis denotes a signal value $x(t)$ of the acoustic signal transmitted at time t. Hereinafter, the acoustic signal transmitted by transmission unit 11 may be called a transmitted acoustic signal.

In step S120, observation unit 12 observes an acoustic signal after the acoustic signal transmitted from transmission unit 11 in step S110 propagates through the part of the user's head. For example, in step S120, microphone 5 detects the acoustic signal propagated from earphone 4. The detected acoustic signal is amplified by microphone amplifier 3, is subjected to A/D conversion in sound processor 2, and is transmitted to information processing device 1.

Figure 4B:
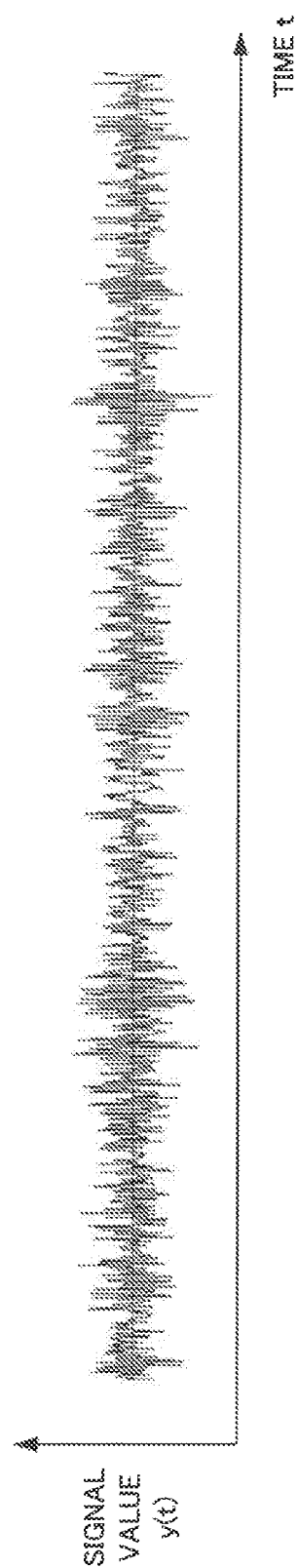
FIG. 4B is a graph illustrating an example of an observed acoustic signal.

FIG. 4B is a graph illustrating an example of the acoustic signal observed by observation unit 12. In the graph of FIG. 4B, a horizontal axis denotes time t and a vertical axis denotes a signal value y(t) of the acoustic signal observed at time t. Hereinafter, the acoustic signal observed by observation unit 12 may be called an observed acoustic signal.

In step S130, calculation unit 13 calculates acoustic characteristics of the part of the user's head from a change in the transmitted acoustic signal and the observed acoustic signal. The acoustic characteristics include, such as, an impulse response, a transfer function obtained by performing Fourier transform or Laplace transform on the impulse response. The acoustic characteristics, for example, include information regarding how the acoustic signal is reflected and/or attenuated in a living body. For example, when earphone 4 and microphone 5 are installed at the entrance of an ear canal and acoustic characteristics that reflect in the ear canal are calculated by calculation unit 13, an ear canal impulse response or an ear canal transfer function may be used as the acoustic characteristics.

FIG. 5 is a graph illustrating an example of the impulse response as the acoustic characteristics calculated by calculation unit 13. In the graph of FIG. 5, a horizontal axis denotes time t and a vertical axis denotes a value g(t) of an impulse response of an acoustic signal observed at time t.

Among the signal value x(t) of the transmitted acoustic signal, the signal value y(t) of the observed acoustic signal, and the value g(t) of the impulse response, there is a relation expressed by the following Equation (1).

[Equation 1]

$$y(t) = \int_0^t x(\tau) g(t-\tau) d\tau \quad (1)$$

Furthermore, among X(f), Y(f), and G(f) obtained by respectively performing Fourier transform on x(t), y(t), and g(t), there is a relation expressed by the following Equation (2). In Equation (2) below, f denotes a frequency band. Furthermore, G denotes a transfer function.

$$Y(f) = G(f) X(f) \quad (2)$$

In step S140, extraction unit 14 extracts a feature amount from the acoustic characteristics calculated by calculation unit 13. As the feature amount, the impulse response or the transfer function may be used as is. That is, extraction unit 14 uses values of each time of the impulse response as the acoustic characteristics or values of each frequency of the transfer function as the feature amount. Furthermore, it is considered to use a feature amount obtained by performing main component analysis and dimensional compression on the impulse response or the transfer function as the acoustic characteristics, or to use mel-frequency cepstrum coefficients (mfcc) disclosed in NPL 1 as a feature amount.

In step S150, identification unit 16 determines whether the extraction of a feature amount this time is the first extraction for a user. As a specific example, identification unit 16 includes a counter memory for counting the number of extractions or searches whether data of a feature amount exists in storage unit 17, thereby performing the above determination. When it is determined as the first extraction, that is, the first registration, the procedure proceeds to step S160, and when it is not determined as the first registration (the second time or more), the procedure proceeds to step S180.

When it is the first registration, storage control unit 15 stores the feature amount extracted in extraction unit 14 in storage unit 17 in step S160. In step S170, when it is detected that the feature amount is present in storage unit 17, service control unit 18 starts an application program for providing a service.

When it is not the first registration, identification unit 16 collates the feature amount obtained by extraction unit 14 with the feature amount of a registered user stored in storage unit 17 in step S180.

In step S190, when the feature amounts coincide with each other as a collation result and it is determined that a user to be authenticated corresponds to a registered user, the procedure proceeds to step S200. When the feature amounts do not coincide with each other as the collation result and it is determined that the user to be authenticated does not correspond to the registered user, the procedure proceeds to step S210. This determination corresponds to one-to-one authentication.

In the one-to-one authentication, feature amounts of a user to be authenticated and a registered user are collated with each other in a one-to-one manner. In such a case, a registered user, for which collation is to be performed, may be designated in advance with a user identification (ID). As a collation method, for example, identification unit 16 may calculate a distance between feature amounts, determine that they are the same person when the distance is smaller than a threshold value, and determine that they are different persons when the distance is larger than the threshold value. As a distance measure, such as the Euclid distance or a cosine distance is considered. However, other distances may be used.

Furthermore, in the above, an example, in which a feature amount stored in advance is stored in storage unit 17, has been described; however, storage unit 17 may store a statistical model instead of the feature amount. The statistical model may be a mean value and a variance value obtained by acquiring a feature amount multiple times for one person, or a relational expression calculated using these values. Alternatively, there are, for example, a Gaussian mixture model (GMM), a support vector machine (SVM), a model using a neutral network, as disclosed in PTL 1.

In step S200, identification unit 16 waits for the passage of a predetermined time (for example, one second) and returns procedure to step S110.

In step S210, service control unit 18, for example, ends an application program providing a service such that the service is not provided to a user who is not a registered user. In such a case, storage control unit 15 may allow storage unit 17 to store a feature amount of an unauthorized user who is not a registered user.

In addition, service control unit 18 may end an application program for a service according to a request from a registered user. Furthermore, when a registered user detaches earphone 4 from his/her ear and thus extraction unit 14 is not able to completely acquire a feature amount (echo sound), service control unit 18 may end the application program for a service. In such a case, identification unit 16 may not immediately but after several times of collation, notify service control unit 18 of a collation result and service stop, after it is found that some reason prevent identification unit 16 from acquiring a feature amount, after several tries.

At the end of the service, service control unit 18 instructs storage control unit 15 to erase data of the feature amount of the registered user in storage unit 17. Storage control unit 15 erase the data of the feature amount of the registered user when the application program is ended.

Thus, the operation of personal authentication device 100 according to the first example embodiment is ended.

According to the first example embodiment of the present invention, it is possible to provide a personal authentication device capable of simply securing security with little psychological and physical burden of a user to be authenticated. In the present example embodiment, personal authentication is performed using a characteristic in which acoustic characteristics of an acoustic signal propagating through a part of a user's head are different for each individual. Since the acoustic characteristics propagating through the part of the user's head are internal characteristics of a living body differently from characteristics observable from an exterior such as a face and a fingerprint, the risk of leakage is low and theft is difficult. Furthermore, in order to know acoustic characteristics, since both the transmitted acoustic signal and the observed acoustic signal are necessary, there is little risk of being acquired and forged by eavesdropping. Furthermore, since an operation to be performed by a user to be authenticated is to wear a headphone or an earphone with an embedded microphone or hold a cellular phone with a microphone embedded in a receiving part to an ear, psychological and physical burden of a user is small. Furthermore, when the personal authentication method of the present example embodiment is used in combination with music distribution, a transceiver, or an information distribution device that transmits voice such as communication, it is possible to provide a user with personal authentication without any additional physical and mental burden.

Furthermore, the acoustic characteristics can be acquired in a short period, such as about one second, and it is possible to keep authenticating a user at all times while a service is being provided. Therefore, as collated with a case where authentication is performed once at the beginning or immediately before receiving any service, when there is an illegal act such as alternation (impersonation) to another person after the authentication, it is possible to detect the illegal act.

Moreover, whenever a service is started, feature amount data of a user is registered in storage unit 17, and whenever the service is ended, the feature amount data registered in storage unit 17 is deleted. In this way, since the feature amount data used as an ID or a password is collated only for a short period of time (only for one-time service use time), it is possible to simply secure high security. Moreover, even though a user with one-ear authentication has a sense of discomfort to an ear used for authentication due to the long-time use of a service and desires to switch the authentication subject to the other ear, it is possible to easily switch the ear to be authenticated. In such a case, it is preferably to perform authentication switching (permission of first authentication by a service administrator) in order to secure security.

Second Example Embodiment

In the first example embodiment of the present invention, personal authentication device 100 is available at all times according to a user's request; however, depending on the content of a service to be provided, an available time (for example, up to 2 hours) or a time zone (for example, between 12:00 to 17:00) of the service may be specified even in the case of the same user. In the second example embodiment of the present invention, a description will be provided for personal authentication device 200 that authenticates a user when an available time is specified.

Figure 6:
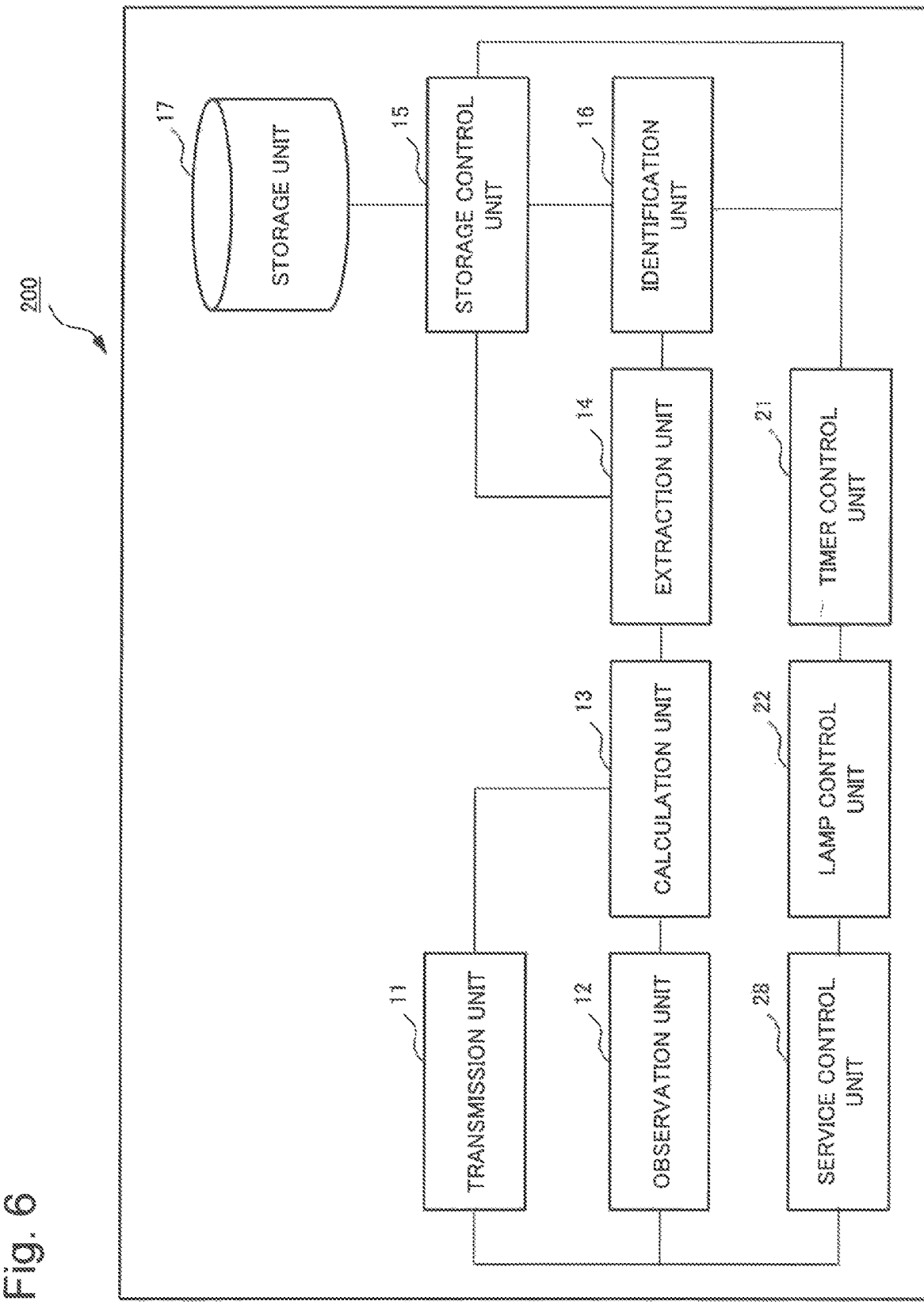
FIG. 6 is a block diagram illustrating a configuration example of a personal authentication device according to a second example embodiment of the present invention.

Personal authentication device 200 according to the second example embodiment of the present invention will be described with reference to the drawings. FIG. 6 is a block diagram illustrating a configuration example of personal authentication device 200 according to the second example embodiment. Personal authentication device 200 includes transmission unit 11, observation unit 12, calculation unit 13, extraction unit 14, storage control unit 15, identification unit 16, storage unit 17, timer control unit 21, lamp control unit 22, and service control unit 28.

Timer control unit 21 controls a timer preset by a service administrator. Specifically, when a time or a time zone preset by the service administrator is passed, timer control unit 21 notifies lamp control unit 22 to change a lamp color. In such a case, timer control unit 21 may notify service control unit 28 to stop the providing service.

Figure 7:
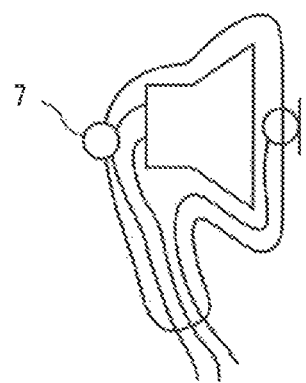
FIG. 7 is a diagram illustrating a configuration example of an earphone and a peripheral device thereof according to a second example embodiment of the present invention.

Lamp control unit 22 controls a color, flickering of a lamp according to the notification from timer control unit 21. As illustrated in FIG. 7, a lamp 7 is installed at a position easily seen from the outside, for example, on the surface of earphone 4. Lamp control unit 22 changes the color of lamp 7 according to a service providing state or a user authentication state. For example, the color of lamp 7 is yellow before first authentication, is green after the first authentication and normal operation, is red in the case of overtime use (time-over) of a registered user, is red flickering when it is determined that it is not used by a registered user.

Figure 8:
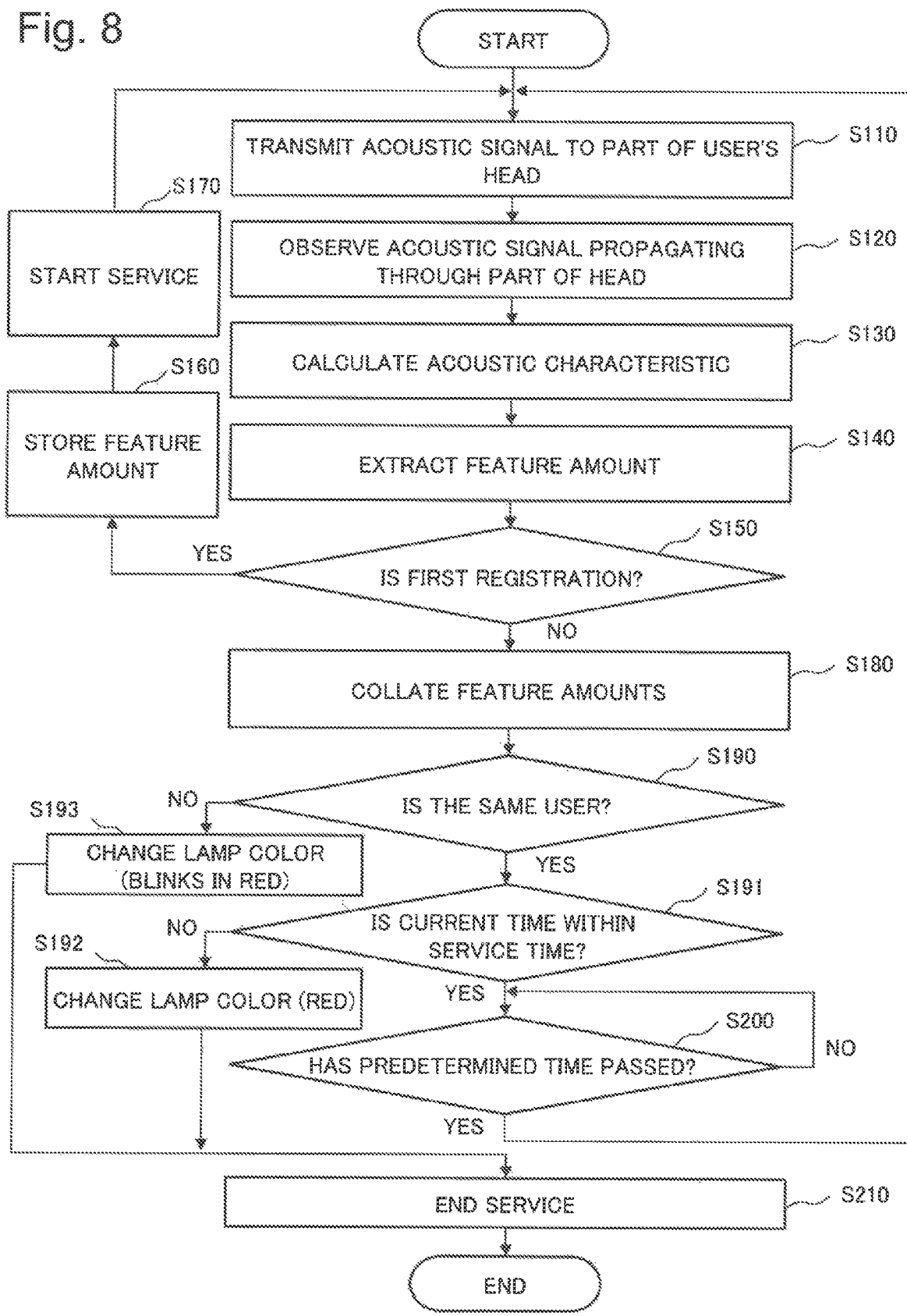
FIG. 8 is a flowchart illustrating an example of an operation of a personal authentication device according to a second example embodiment of the present invention.

The operation of personal authentication device 200 according to the second example embodiment will be described with reference to the flowchart of FIG. 8.

Steps S110 to S180 are the same as those of the operation of the first example embodiment (see FIG. 3).

In step S190, when it is determined that a user to be authenticated corresponds to a registered user as the collation result, the procedure proceeds to step S191. When it is determined that the user to be authenticated does not correspond to the registered user, the procedure proceeds to step S193. In step S193, lamp control unit 22 changes the color of lamp 7 being currently displayed (for example, it blinks in red).

In step S191, timer control unit 21 determines whether a current time exceeds a time (a service time) preset by a service administrator. When the current time is within the service time, the procedure proceeds to step S200, and when the current time is out of the service time, the procedure proceeds to step S192. In step S192, lamp control unit 22 changes the color of lamp 7 being currently displayed (for example, it blinks in red). Timer control unit 21 notifies lamp control unit 22 such that the lamp color is changed. In such a case, timer control unit 21 may notify service control unit 28 such that a service is stopped.

Steps S200 and S210 are the same as those of the operation of the first example embodiment (see FIG. 3).

Thus, the operation of personal authentication device 200 according to the second example embodiment is ended.

According to the second example embodiment of the present invention, it is possible to provide a personal authentication device with little psychological and physical burden of a user to be authenticated and with high security performance. Moreover, in addition to the effects of the first example embodiment, when a user uses a service for a predetermined time or more or when a user uses a service out of a specified time, the color of the lamp is changed. In this way, it is possible to allow a service administrator to visibly recognize the use of a service by a user out of a specified time. Furthermore, when a user uses a service for a predetermined time or more, personal authentication device 200 may stop providing the service. In this way, a service administrator can more accurately manage personal authentication device 200.

In addition, instead of flickering the lamp, a sound buzzer may also be used. Moreover, even in the case of a legally authorized user, when it is intended to prohibit use out of a specified place, it is also possible to manage (monitor) a place of use by using such as a beacon system when the user is indoors or by using such as a global positioning system (GPS) system when the user is outdoors. The management of a person to use, a use time, and a place of use may be realized by any combination.

Third Example Embodiment

Figure 9:
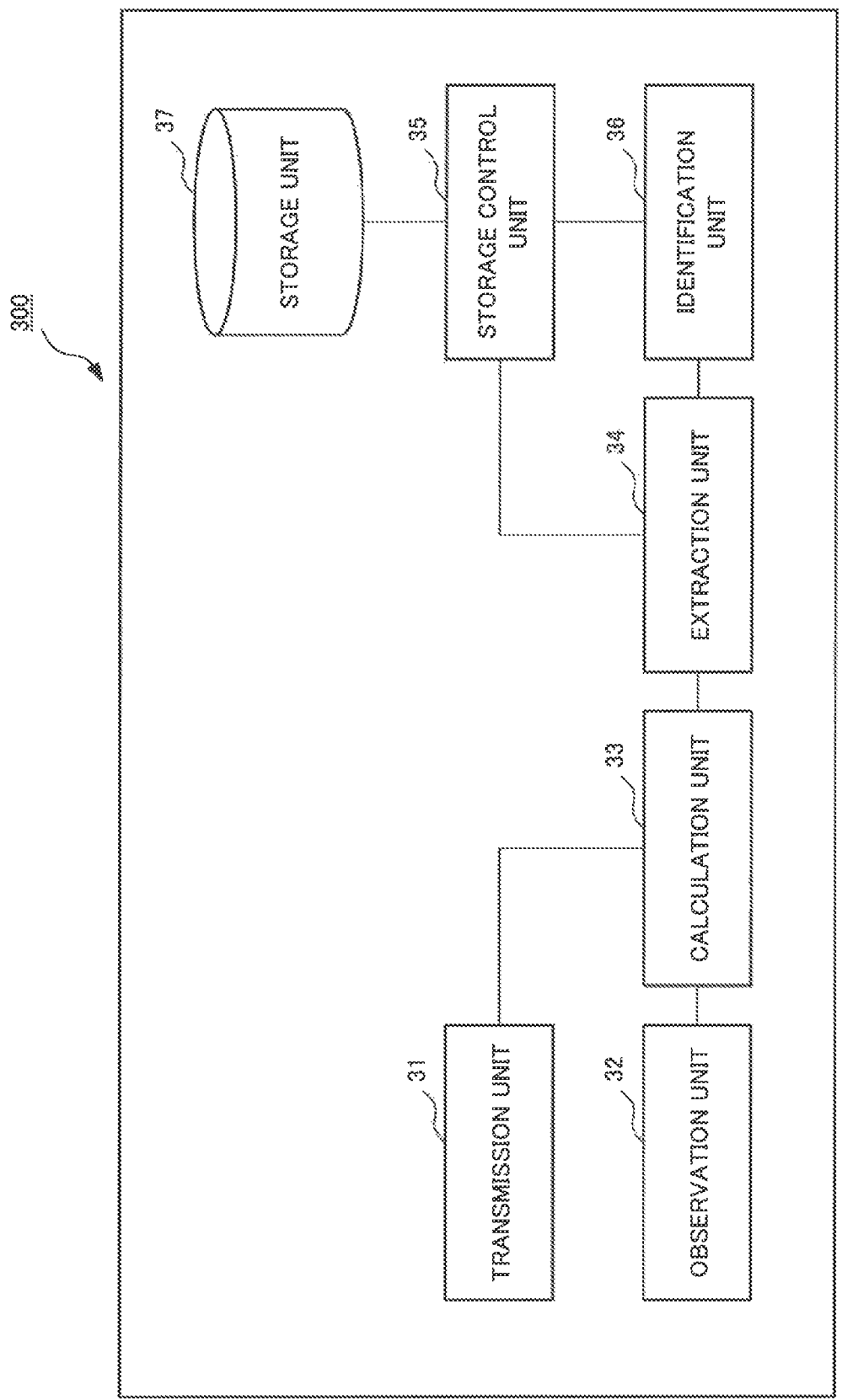
FIG. 9 is a block diagram illustrating a configuration example of a personal authentication device according to a third example embodiment of the present invention.

Personal authentication device 300 according to a third example embodiment of the present invention includes transmission unit 31, observation unit 32, calculation unit 33, extraction unit 34, storage control unit 35, identification unit 36, and storage unit 37 as illustrated in FIG. 9.

Transmission unit 31 transmits a first acoustic signal to a part of a user's head. Observation unit 32 observes a second acoustic signal that is an acoustic signal after the first acoustic signal propagates through the part of the user's head. Calculation unit 33 calculates acoustic characteristics from the first acoustic signal and the second acoustic signal. Extraction unit 34 extracts a feature amount related to a user from the acoustic characteristics. Storage control unit 35 registers the feature amount in the storage unit as a first feature amount. Identification unit 36 identifies the user by collating the first feature amount acquired from the storage unit with a second feature amount acquired after the extraction of the first feature amount from the extraction unit. Storage unit 37 stores the first feature amount. It should be noted that when identification unit 36 identifies the user as being identical, transmission unit 31 transmits the first acoustic signal every predetermined interval.

According to the third example embodiment of the present invention, it is possible to provide a personal authentication with little psychological and/or physical burden of a user to be authenticated and with high security performance. The reason for this is because identification unit 36 identifies a user by collating the first feature amount registered in the storage unit for the first time with the second feature amount acquired after the first registration and transmission unit 31 transmits the first acoustic signal every predetermined interval when identification unit 36 identifies the user as being identical. In this way, a user simply wears an earphone, so that it is possible to perform personal authentication with high security performance at all times.

(Configuration of Information Processing Device)

Figure 10:
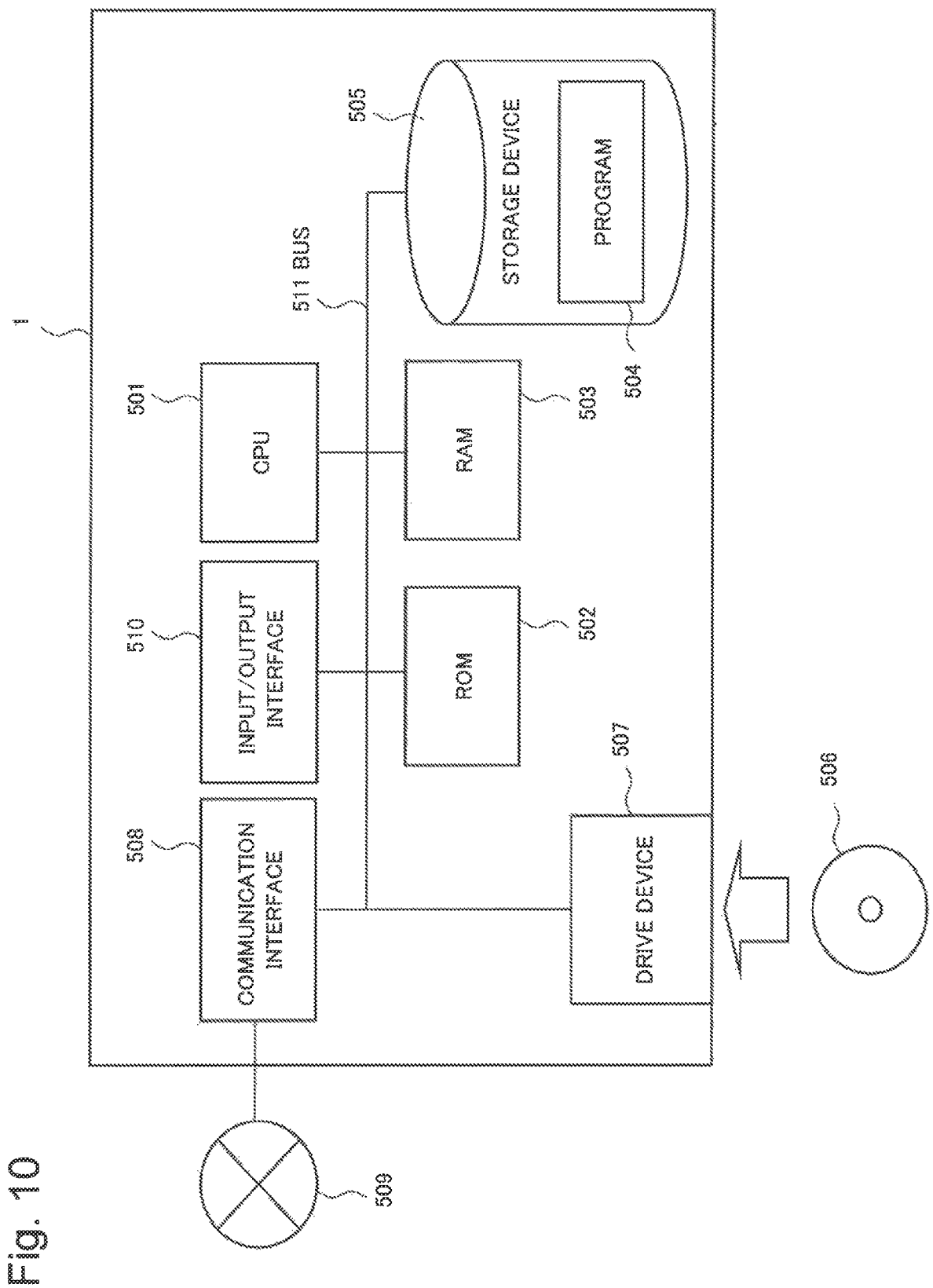
FIG. 10 is a configuration example of an information processing device for embodying each example embodiment according to the present invention.

In the aforementioned each example embodiment of the present invention, respective elements of respective personal authentication devices illustrated in FIG. 1, FIG. 6, and FIG. 9 illustrate blocks of a functional unit. Some or all of respective elements of the personal authentication devices, for example, are realized using an arbitrary combination of information processing device 1 as illustrated in FIG. 10 and a program. Information processing device 1 includes the following elements as an example.

Central processing unit (CPU) 501
Read only memory (ROM) 502
Random access memory (RAM) 503
Program 504 loaded on RAM 503
Storage device 505 storing program 504
Drive device 507 for performing reading and writing of recording medium 506
Communication interface 508 connected to communication network 509
Input/output interface 510 for performing input/output of data
Bus 511 connecting each element Respective elements of the personal authentication device in each example embodiment of the present invention are implemented when CPU 501 acquires and executes program 504 for performing functions of the elements. Program 504 for performing the functions of the elements of the personal authentication device, for example, is stored in storage device 505 or RAM 503 in advance and is read by CPU 501 when necessary. It should be noted that program 504 may be supplied to CPU 501 via communication network 509, or drive device 507 may read program 504 stored in recording medium 506 in advance and supply CPU 501 with read program 504.

There are various modification examples in the implementation method of each device. For example, the personal authentication device may be implemented by an arbitrary combination of different information processing devices and programs for each element. Furthermore, a plurality of elements included in the personal authentication device may be implemented by an arbitrary combination of one information processing device 1 and a program.

Furthermore, some or all of respective elements of respective personal authentication devices are implemented by other general-purpose or dedicated circuits, processors or a combination thereof. These may also be configured by a single chip, or by a plurality of chips connected via a bus.

Some or all of respective elements of respective personal authentication devices may be implemented by a combination of the aforementioned circuits and a program.

When some or all of respective elements of respective personal authentication devices are implemented by a plurality of information processing devices, circuits, the plurality of information processing devices, circuits may be arranged in a concentrated manner or arranged in a distributed manner. For example, the information processing devices, circuits may be implemented as a form in which a client and server system, a cloud computing system are connected to one another via a communication network.

Some or all of the aforementioned example embodiments are also described in the following Supplementary Notes; however, the present invention is not limited thereto.

Supplementary Note 1

A personal authentication device comprising:
a transmission means for transmitting a first acoustic signal to a part of a head of a user;
an observation means for observing a second acoustic signal that is an acoustic signal after the first acoustic signal propagates through the part of the head of the user;
a calculation means for calculating acoustic characteristics from the first acoustic signal and the second acoustic signal;
an extraction means for extracting a feature amount related to the user from the acoustic characteristics;
a storage control means for registering the feature amount in a storage means as a first feature amount; and
an identification means for identifying the user by collating the first feature amount registered in the storage means with a second feature amount extracted from the extraction means after the first feature amount is registered, wherein, when the identification means identifies the user as being identical, the transmission means transmits the first acoustic signal every predetermined interval.

Supplementary Note 2

The personal authentication device according to Supplementary note 1, further comprising:
a service control means for providing a service to the user when the identification means identifies the user as being identical.

Supplementary Note 3

The personal authentication device according to Supplementary note 1 or 2, wherein, when the identification means is not able to identify the user as being identical, the service control means stops providing the service and the storage control means deletes the first feature amount registered in the storage means.

Supplementary Note 4

The personal authentication device according to any one of Supplementary notes 1 to 3, further comprising:
a light emitting means for emitting light in a color different from a color when the user is identified as being identical in a case where the identification means is not able to identify the user as being identical.

Supplementary Note 5

The personal authentication device according to any one of Supplementary notes 1 to 4, further comprising:
a timer means for detecting whether a specified time has passed,
when the identification means identifies the user as being identical and the timer means detects that the specified time has passed, the service control means stops providing the service to the user.

Supplementary Note 6

The personal authentication device according to any one of Supplementary notes 1 to 5, wherein, when the timer means detects that the specified time has passed, the light emitting means emits light in a color different from a color when the timer means detects that the specified time has not passed.

Supplementary Note 7

A personal authentication method comprising:
transmitting a first acoustic signal to a part of a head of a user;
observing a second acoustic signal that is an acoustic signal after the first acoustic signal propagates through the part of the head of the user;
calculating acoustic characteristics from the first acoustic signal and the second acoustic signal;
extracting a feature amount related to the user from the acoustic characteristics;
registering the feature amount in a storage means as a first feature amount; and
identifying the user by collating the first feature amount registered in the storage means with a second feature amount extracted after the first feature amount is registered,
wherein, when the user is identified as being identical, the first acoustic signal is transmitted every predetermined interval.

Supplementary Note 8

The personal authentication method according to Supplementary note 7, further comprising:
providing a service to the user when the user is identified as being identical.

Supplementary Note 9

The personal authentication method according to Supplementary note 7 or 8, wherein, when the user is not identified as being identical, providing of the service is stopped and the first feature amount registered in the storage means is deleted.

Supplementary Note 10

The personal authentication method according to any one of Supplementary notes 7 to 9, further comprising:
emitting, by a light emitting means, light in a color different from a color when the user is identified as being identical in a case where it is not possible to identify the user as being identical.

Supplementary Note 11

The personal authentication method according to any one of Supplementary notes 7 to 10, further comprising:
detecting whether a specified time has passed,
when the user is identified as being identical and it is detected that the specified time has passed, providing of the service to the user is stopped.

Supplementary Note 12

The personal authentication method according to any one of Supplementary notes 7 to 11, wherein, when it is detected that the specified time has passed, the light emitting means emits light in a color different from a color when the specified time has not passed.

Supplementary Note 13

A recording medium stored with a personal authentication program causing a computer to perform:
transmitting a first acoustic signal to a part of a head of a user;
observing a second acoustic signal that is an acoustic signal after the first acoustic signal propagates through the part of the head of the user;
calculating acoustic characteristics from the first acoustic signal and the second acoustic signal;
extracting a feature amount related to the user from the acoustic characteristics;
registering the feature amount in a storage means as a first feature amount; and
identifying the user by collating the first feature amount registered in the storage means with a second feature amount extracted after the first feature amount is registered, wherein, when the user is identified as being identical, the first acoustic signal is transmitted every predetermined interval.

Supplementary Note 14

The recording medium according to Supplementary note 13, further comprising:
providing a service to the user when the user is identified as being identical.

Supplementary Note 15

The recording medium according to Supplementary note 13 or 14, wherein, when the user is not identified as being identical, providing of the service is stopped and the first feature amount registered in the storage means is deleted.

Supplementary Note 16

The recording medium according to any one of Supplementary notes 13 to 15, further comprising:
emitting, by a light emitting means, light in a color different from a color when the user is identified as being identical in a case where it is not possible to identify the user as being identical.

Supplementary Note 17

The recording medium according to any one of Supplementary notes 13 to 16, further comprising:
detecting whether a specified time has passed,
when the user is identified as being identical and it is detected that the specified time has passed, providing of the service to the user is stopped.

Supplementary Note 18

The recording medium according to any one of Supplementary notes 13 to 17, wherein, when it is detected that the specified time has passed, the light emitting means emits light in a color different from a color when the specified time has not passed.

So far, the present invention has been described with reference to the present example embodiments and the examples; however, the present invention is not limited to the aforementioned example embodiments and examples. Various modifications which can be understood by a person skilled in the art can be made in the configuration and details of the present invention within the scope of the present invention.

REFERENCE SIGNS LIST

1 information processing device
2 sound processor
3 microphone amplifier
4 earphone
5 microphone
6 user
7 lamp
11 transmission unit
12 observation unit
13 calculation unit
14 extraction unit
15 storage control unit
16 identification unit
17 storage unit
18 service control unit
21 timer control unit
22 lamp control unit
28 service control unit
31 transmission unit
32 observation unit
33 calculation unit
34 extraction unit
35 storage control unit
36 identification unit
37 storage unit
100 personal authentication device
200 personal authentication device
300 personal authentication device
500 information processing device
501 CPU
503 RAM
504 program
505 storage device
506 recording medium
507 drive device
508 communication interface
509 communication network
510 input/output interface
511 bus

The invention claimed is:
1. A personal authentication device comprising:
one or more memories storing instructions and registering a second feature amount; and
one or more processors configured to process the instructions to:
output a first acoustic signal to earphone, the first acoustic signal being signal for sound is transmitted from the earphone;
receive a second acoustic signal from the earphone, the second acoustic signal being signal based on echo sound being the sound echoed in an ear of the user;
calculate a first feature amount related to the user based on the second acoustic signal;
collate the first feature amount with the second feature amount; and
output a third acoustic signal being different from the first acoustic signal to the earphone based on a collation result, wherein
the one or more processors is configured to process the instructions to:
recognize the user as user authorized to use the earphone based on the collation result;
provide a service to the user when the collation result indicate coincidence;
when the collation result does not indicate the coincidence, providing of the service is stopped and the second feature amount registered within the one or more memories is deleted from the one or more memories; and
detect whether a specified time has passed,
when the collation result indicate coincidence and it is detected that the specified time has passed, the providing of the service to the user is stopped.
2. A personal authentication method comprising:
outputting a first acoustic signal to earphone, the first acoustic signal being signal for sound is transmitted from the earphone;
receiving a second acoustic signal from the earphone, the second acoustic signal being signal based on echo sound being the sound echoed in an ear of the user;

calculating a first feature amount related to the user based on the second acoustic signal;

collating the first feature amount with a second feature amount registered with one or more memories; and outputting a third acoustic signal being different from the first acoustic signal to the earphone based on a collation result, wherein the personal authentication method comprises:

recognizing the user as user authorized to use the earphone based on the collation result;

providing a service to the user when the collation result indicate coincidence;

when the collation result does not indicate the coincidence, providing of the service is stopped and the second feature amount registered within the one or more memories is deleted from the one or more memories; and detecting whether a specified time has passed, when the collation result indicate coincidence and it is detected that the specified time has passed, the providing of the service to the user is stopped.

3. A non-transitory computer readable recording medium stored with a personal authentication program causing a computer to perform:

outputting a first acoustic signal to earphone, the first acoustic signal being signal for sound is transmitted from the earphone;

receiving a second acoustic signal from the earphone, the second acoustic signal being signal based on echo sound being the sound echoed in an ear of the user;

calculating a first feature amount related to the user based on the second acoustic signal;

collating the first feature amount with a second feature amount registered with one or more memories; and outputting a third acoustic signal being different from the first acoustic signal to the earphone based on a collation result, wherein the personal authentication program causes the computer to perform:

recognizing the user as user authorized to use the earphone based on the collation result;

providing a service to the user when the collation result indicate coincidence;

when the collation result does not indicate the coincidence, providing of the service is stopped and the second feature amount registered within the one or more memories is deleted from the one or more memories; and detecting whether a specified time has passed, when the collation result indicate coincidence and it is detected that the specified time has passed, the providing of the service to the user is stopped.

* * * * *